United States Patent
Govari et al.

(10) Patent No.: US 11,771,488 B2
(45) Date of Patent: Oct. 3, 2023

(54) ABLATION OF LESIONS OF LOW-MEDIUM DEPTHS USING ULTRAHIGH RADIOFREQUENCY (RF) POWER FOR ULTRASHORT DURATIONS

(71) Applicant: BIOSENSE WEBSTER (ISRAEL) LTD., Yokneam (IL)

(72) Inventors: Assaf Govari, Haifa (IL); Andres Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 597 days.

(21) Appl. No.: 16/658,601

(22) Filed: Oct. 21, 2019

(65) Prior Publication Data

US 2021/0113259 A1    Apr. 22, 2021

(51) Int. Cl.
| | | |
|---|---|---|
| A61B 18/12 | (2006.01) | |
| A61B 18/14 | (2006.01) | |
| A61B 90/00 | (2016.01) | |
| A61B 17/00 | (2006.01) | |
| A61B 18/00 | (2006.01) | |

(52) U.S. Cl.
CPC ...... *A61B 18/1206* (2013.01); *A61B 18/1492* (2013.01); *A61B 2017/0019* (2013.01); *A61B 2018/00351* (2013.01); *A61B 2018/00577* (2013.01); *A61B 2018/00642* (2013.01);
(Continued)

(58) Field of Classification Search
CPC ............ A61B 18/1206; A61B 18/1492; A61B 2017/0019; A61B 2018/00351; A61B 2018/00577; A61B 2018/00642; A61B 2018/00761; A61B 2018/00791; A61B 2090/065; A61B 34/20; A61B 2018/00702; A61B 2018/00714; A61B 2018/00988; A61B 2018/00779; A61B 2018/00886; A61B 18/12
See application file for complete search history.

(56) References Cited

U.S. PATENT DOCUMENTS 6,156,031 A * 12/2000 Aita .................. A61B 18/1492
606/41
9,962,217 B2 * 5/2018 Govari .................. A61B 18/12
(Continued)

FOREIGN PATENT DOCUMENTS

WO    WO-2015192027 A1 * 12/2015 ......... A61B 18/1206
WO    WO 2018/006086 A1    1/2018

OTHER PUBLICATIONS

Extended European Search Report dated Mar. 4, 2021, for Application No. 20202735.5, 8 pages.

*Primary Examiner* — Linda C Dvorak
*Assistant Examiner* — Mystee Nguyen Delgado
(74) *Attorney, Agent, or Firm* — Lewis Roca Rothgerber Christie LLP

(57) ABSTRACT

A method of body tissue ablation includes defining an ultrahigh-power ultrashort-duration (UPUD) ablation protocol that specifies an ablation signal having (i) a target ablation power of at least 400 Watts and (ii) a pulse duration that does not exceed three seconds, for creating a specified lesion in tissue in a body of a patient. Contact is made between an ablation probe and the tissue. Using the ablation probe, the ablation signal is applied to the tissue according to the UPUD protocol, which delivers the ablation signal having the specified target ablation power and duration.

16 Claims, 2 Drawing Sheets

(52) U.S. Cl.
CPC ............... *A61B 2018/00761* (2013.01); *A61B 2018/00791* (2013.01); *A61B 2090/065* (2016.02)

(56) References Cited

U.S. PATENT DOCUMENTS

| | | | |
|---|---|---|---|
| 10,322,286 | B2 | 6/2019 | Viswanathan et al. |
| 10,405,920 | B2 | 9/2019 | Govari et al. |
| 10,471,254 | B2* | 11/2019 | Sano ........................ A61N 1/08 |
| 10,512,779 | B2* | 12/2019 | Viswanathan ......... A61N 1/362 |
| 11,452,563 | B2 | 9/2022 | Govari et al. |
| 2003/0199864 | A1* | 10/2003 | Eick ................... A61B 18/1492 606/41 |
| 2004/0172110 | A1 | 9/2004 | Satake |
| 2008/0097429 | A1 | 4/2008 | McClurken |
| 2009/0093802 | A1 | 4/2009 | Kulesa |
| 2012/0053581 | A1* | 3/2012 | Wittkampf ......... A61B 18/1492 606/41 |
| 2014/0257069 | A1* | 9/2014 | Eliason .................... A61B 5/24 600/373 |
| 2015/0320481 | A1* | 11/2015 | Cosman, Jr. ........... A61B 34/10 606/35 |
| 2016/0066984 | A1* | 3/2016 | Janssen .............. A61B 18/1477 606/34 |
| 2017/0065329 | A1 | 3/2017 | Benamou et al. |
| 2018/0289284 | A1* | 10/2018 | Panescu ................. A61B 5/287 |

* cited by examiner

ABLATION OF LESIONS OF LOW-MEDIUM DEPTHS USING ULTRAHIGH RADIOFREQUENCY (RF) POWER FOR ULTRASHORT DURATIONS

FIELD OF THE INVENTION

The present invention relates generally to radiofrequency (RF) ablation, and particularly to cardiac RF ablation.

BACKGROUND OF THE INVENTION

Techniques for optimizing radiofrequency (RF) ablation treatments were previously proposed in patent literature. For example, U.S. Patent Application Publication 2009/0093802 describes systems and methods for transeptal cardiac procedures. A method for treating a patient in accordance with a particular embodiment includes positioning a tissue penetrating guidewire adjacent to a cardiac septum, directing pulses of energy to the guidewire, and advancing the guidewire into and through the septum by moving the guidewire in a distal direction in a series of discrete steps. Individual steps can be of a predetermined distance measured outside the patient's body. The method can further include passing a catheter over the guidewire after the guidewire has passed through the septum.

As another example, U.S. Patent Application Publication 2004/0172110 describes an RF heating balloon catheter that is capable of cauterizing a target lesion in an atrial vestibule. The RF heating balloon catheter comprises an inflatable balloon capable of coming into contact with a target lesion when inflated, an RF electrode serving as a counter to a surface electrode attached to a surface of a subject's body and being placed in a wall of the balloon or inside the balloon to supply RF power between the surface electrode and the RF electrode, a temperature sensor capable of sensing temperature inside the balloon, a guide shaft projecting from the extremity of the inner tube and capable of holding the balloon on the target lesion, and a guidewire extended through the catheter tube and the guide shaft.

U.S. Pat. No. 9,962,217 describes tissue ablation systems and methods in which a cardiac catheter incorporates a pressure detector for sensing a mechanical force against the distal tip when engaging an ablation site. Responsively to the pressure detector, a controller computes an ablation volume according to relationships between the contact pressure against the site, the power output of an ablator, and the energy application time. The system applies a specified dosage of energy for an application time and at a power level to the tissue for ablation thereof, wherein at least one of the application time of the dosage and the power level depend on the mechanical force.

SUMMARY OF THE INVENTION

An embodiment of the present invention provides a method of body tissue ablation, the method including defining an ultrahigh-power ultrashort-duration (UPUD) ablation protocol that specifies an ablation signal having (i) a target ablation power of at least 400 Watts and (ii) a pulse duration that does not exceed three seconds, for creating a specified lesion in tissue in a body of a patient. Contact is made between an ablation probe and the tissue. Using the ablation probe, the ablation signal is applied to the tissue according to the UPUD protocol, which delivers the ablation signal having the specified target ablation power and duration.

In some embodiments, defining the UPUD ablation protocol includes setting the pulse duration to not exceed one second. In other embodiments, defining the UPUD ablation protocol includes setting the pulse duration to not exceed a single heartbeat period of the patient.

In an embodiment, the method further includes, during application of the ablation signal, monitoring a temperature in a vicinity of the tissue, and if the monitored temperature exceeds a predefined maximal temperature, halting the ablation signal.

In another embodiment, the method further includes, during application of the ablation signal, monitoring a contact force that the probe exerts on the tissue, and if the monitored contact force falls below a prespecified value, halting the ablation signal.

There is additionally provided, in accordance with an embodiment of the present invention, a system for body tissue ablation, the system including a memory, an ablation probe, an ultrahigh-power ultra-short-duration (UPUD) generator, and a processor. The memory is configured to store values of an ultrahigh-power ultrashort-duration (UPUD) ablation protocol that specifies an ablation signal having (i) a target ablation power of at least 400 Watts and (ii) a pulse duration that does not exceed three seconds, for creating a specified lesion in tissue in a body of a patient. The ablation probe is configured to make contact with the tissue. The UPUD generator is configured to generate the ablation signal. The processor is configured to control the generator and the ablation probe to apply the ablation signal to the tissue according to the UPUD protocol, which delivers the ablation power having the specified target ablation power and duration.

The present invention will be more fully understood from the following detailed description of the embodiments thereof, taken together with the drawings in which:

DETAILED DESCRIPTION OF EMBODIMENTS

Overview

Figure 1:
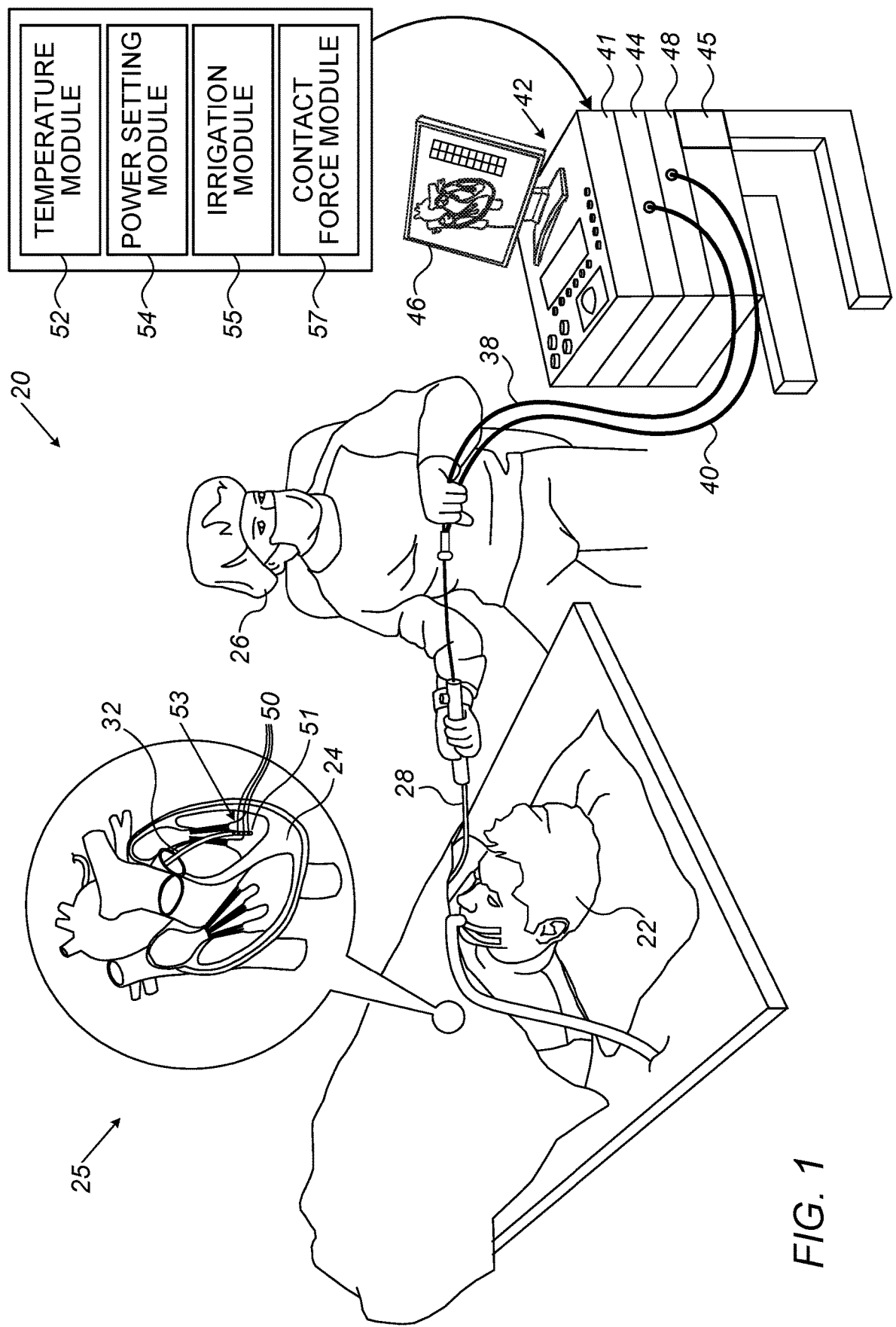
FIG. 1 is a schematic, pictorial illustration of a system for ultrahigh-power ultrashort-duration (UPUD) cardiac radiofrequency (RF) ablation therapy, in accordance with an embodiment of the present invention.

Cardiac radiofrequency (RF) ablation systems may vary the rate of ablative power during ablation in an attempt to achieve an exact lesion depth. Some systems may vary both the RF power and irrigation rate, as well as the time duration of ablation, while ensuring that the temperature of the ablated tissue does not exceed a maximum value or falls below a minimal value.

However, during ablation of, for example, thin tissues, the tissue may have poor temperature response (e.g., tissue temperature may rise/fall unexpectedly). As a result, the system may correspondingly vary the amount of energy it applies to tissue, which may result in an uncontrolled lesion depth. For example, in typical protocols that apply several tens of watts for a time duration up to ten seconds, an uncontrolled conductive heating mechanism in the tissue may cause an uncontrolled lesion depth.

In some cases, other control readings, such as impedances, may be inaccurate, leading to incorrect tuning of RF power and duration of ablation, such as applying too little power for too long a time, resulting in inefficient ablation and possible side effects, such as blood clots.

Embodiments of the present invention that are described hereinafter operate an ablation system in a constant ultra-high-power ultrashort-duration (UPUD) mode. Typically, the disclosed UPUD ablation protocols use an ultrahigh rating of ablating RF power (e.g., at least 400 watts per ablating electrode) that is applied to tissue for ultrashort time duration (e.g., no more than three seconds and typically only for sub-second durations of 0.5-0.9 seconds, depending on target lesion depth) to achieve a preplanned lesion. The ultrashort ablation time ensures that the high power is concentrated in the desired lesion area, so as to considerably reduce risk of collateral damage from energy that escapes the desired area, for example damage caused by conductive heating via tissue.

With the disclosed UPUD-mode of RF ablation the resulting lesion depth mainly depends on the resistive heating of the tissue and not the conductive heating of tissue, so as to achieve high level of reproducibility of lesion parameters. In particular, the difference between the aforementioned conventional ablation protocols and the disclosed UPUD protocols is significant especially in areas where it is hard to maintain a stable position of the catheter, for example, at a ridge between a pulmonary vein and an appendage.

The capability to generate and apply RF ablation in a time duration comparable with a single heartbeat significantly reduces requirements over catheter stability for long duration (e.g., for ten heartbeats). The relaxed requirement, in turn, reduces the effort and time a physician needs to spend in order to stabilize the catheter for achieving an accurate, effective lesion. In an embodiment, the RF ablation duration is set to not exceed a single heartbeat period (a single cardiac cycle) of the patient. The heartbeat period may be pre-measured for the particular patient, or a general upper bound suitable for all patients can be set.

In some embodiments, a processor running an algorithm during the ablation monitors the temperature, and, if temperature exceeds an allowable maximal temperature value (e.g., a prespecified high temperature limit) the processor halts the ablation procedure. Additionally or alternatively, during the ablation the processor monitors contact force between catheter and tissue, and if contact force falls below a prespecified value, which causes ablation efficiency to fall, the processor halts the ablation procedure.

With multi-electrode catheters, embodiments of the invention are able to apply approximately 400 watts for each of the electrodes for a typical required time duration being, as noted above, in the sub-second range. The disclosed UPUD ablation can produce, for example, a ring of accurate lesions that are highly localized.

The disclosed UPUD RF ablation technique may thus improve the clinical outcome of catheter-based RF ablation procedures.

System Description

FIG. 1 is a schematic, pictorial illustration of a system 20 for ultrahigh-power ultrashort-duration (UPUD) cardiac radiofrequency (RF) ablation therapy, in accordance with an embodiment of the present invention. Typically, a memory 45 of system 20 stores numerous ablation protocols for different clinical scenarios, such as the protocol described in FIG. 2.

As seen, a physician 26 inserts a catheter 28 through a blood vessel into a chamber of a heart 24 of a subject 22, and manipulates the catheter so that a distal end 32 of the catheter contacts cardiac tissue in an area that is to be treated. A tip electrode 51 of catheter 28, seen in inset 25, comprises one or more temperature sensors 50, which measure the temperature of the electrode. In some embodiments this temperature is used to estimate the temperature in the vicinity of the ablated tissue. Tip electrode 51 further comprises one or more contact force sensors 53, which measure a force exerted by tip electrode 51 on tissue.

A method to estimate an instantaneous contact force exerted by an ablation probe against the tissue is described in U.S. patent application Ser. No. 16/403,865, filed May 6, 2019, entitled "Adapting Irrigation rate in Radiofrequency (RF) Ablation in Response to Contact-Force Variation," which is assigned to the assignee of the present patent application and whose disclosure is incorporated herein by reference. Alternatively, any other suitable technique can be used for estimating the contact force exerted by tip electrode 51 on the tissue.

After positioning distal end 32 at an ablation site, and ensuring that the tip is in contact with cardiac tissue, operator 26 actuates an ultrahigh-power ultrashort-duration (UPUD) RF energy generator 44 in a control console 42 to supply RF power via a cable 38 to distal end 32. Meanwhile, an irrigation pump 48 supplies a cooling fluid, such as normal saline solution, via a tube 40 and a lumen in catheter 28 to the distal end. Typically, both before and during the ablation, a display 46 displays values of the ablation parameters, such as those listed in Tables I-II below, to physician 26.

Timing ultrahigh-power ultrashort-duration (UPUD) RF and irrigation may be coordinated in order to give the appropriate volume of irrigation during the ultrashort ablation, so as to cool the tip of the catheter and the tissue without overloading the heart with excessive irrigation fluid.

In order to operate system 20, a processor 41 includes a number of modules used by the processor to operate the system. These modules comprise a temperature module 52, a power setting module 54, an irrigation module 55, and a contact force module 57, the functions of which are described below. In particular, processor 41 runs a dedicated algorithm as disclosed herein, included in FIG. 2, which enables processor 41 to perform the disclosed steps, as further described below.

Figure 2:
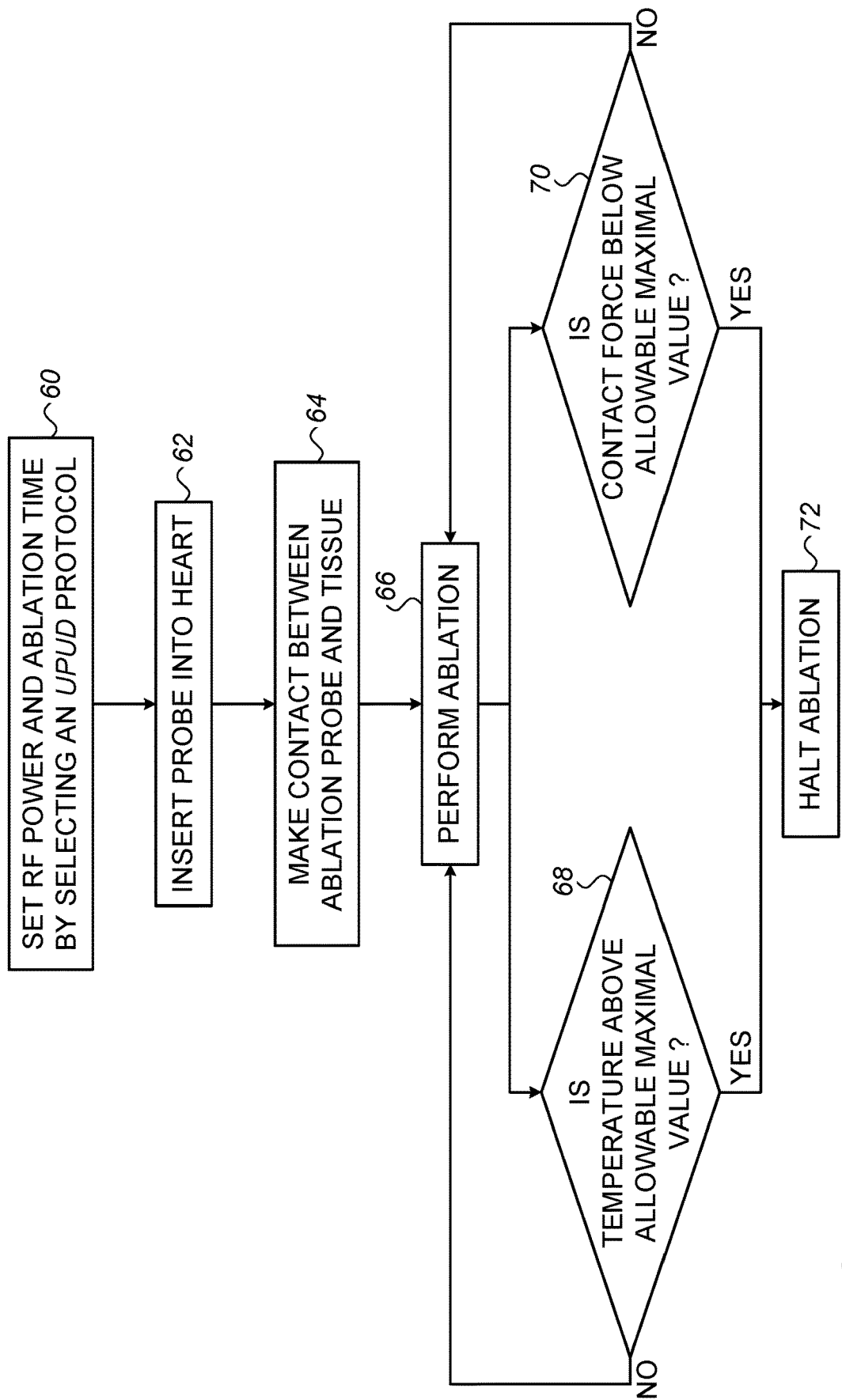
FIG. 2 is a flow chart that schematically illustrates steps of an algorithm performed in the operation of the ultrahigh-power ultrashort-duration (UPUD) RF ablation system of FIG. 1, according to an embodiment of the present invention.

Although the pictured embodiment relates specifically to the use of a tip ablation device for ablation of heart tissue, the methods described herein may alternatively be applied in ablation devices comprising multiple ablation electrodes where each electrode is independently controlled by processor 41 and operates according to RF power and duration specified in UPUD protocols, such as described in FIG. 2.

Applying Ultrahigh RF Power for Ultrashort Durations

FIG. 2 is a flow chart that schematically illustrates steps of an algorithm performed in operation of ultrahigh-power ultrashort-duration (UPUD) RF ablation system 20 of FIG. 1, according to an embodiment of the present invention. The process begins at an ablation parameter presetting step 60, in which physician 26 presets ablation power and time duration. Step 60 may involve generating different protocols for different clinical scenarios, and storing the protocols, for example, in memory 45 of system 20.

In some embodiments, the aforementioned ablation parameters, and other preset paraments, are set as shown in Tables I-II. Typically, for the RF power per electrode, an operator of the system only sets the ultrahigh RF power, while a minimal RF power is automatically set by the system to zero for safety reasons.

Tables I-II bring different possible settings that may be used to optimize lesion depth and minimize collateral damage, depending on the clinical need.

TABLE I

Low Lesion Depth

| Parameter | Value/Range |
| --- | --- |
| Preset ablation power level | 400 W |
| Preset ablation time | 0.5 s-0.7 s |
| Allowable maximal temperature | 65° C. |
| Sampling rate of contact force | 5 Hz-70 Hz |
| Preset irrigation flow rate | 2-30 ml/min |

TABLE II

Medium Lesion Depth

| Parameter | Value/Range |
| --- | --- |
| Preset ablation power level | 400 W |
| Preset ablation time | 0.8 s-0.9 s |
| Allowable maximal temperature | 65° C. |
| Sampling rate of contact force | 5 Hz-70 Hz |
| Irrigation flow rate | 2-30 ml/min |

Ablation parameters setting step 60 is implemented before physician 26 performs an ablation, e.g., by using or modifying a predefined UPUD ablation protocol.

At the beginning of an ablation session, in a probe introduction step 62, physician 26 inserts catheter 28 into a desired location in heart 24, using a catheter position tracking system incorporated into system 20.

Next, physician 26 makes physical contact between electrode tip 51 and target cardiac tissue, at an electrode-tissue contact step 64. Processor 41 receives contact-force indicative signals from sensors on catheter 28 and determines the instantaneous contact force.

At RF delivery step 66, physician 26 operates system 20, with a particular ablation protocol that physician 26 selected, for which the parameter values were selected in steps 60 and 62. The task of physician 26 is to perform the preset ablation protocol by applying (e.g., with electrode 51) the target rate of power during the ultrashort time duration defined, for example, in UPUD protocols comprising ablation parameters shown in Tables I-II.

The values given in Tables I-II are example values, and any other suitable values can be used in alternative embodiments. Generally, the power level applied per electrode is at least 400 W, and the pulse duration does not exceed three seconds. In most practical implementations, the pulse duration does not exceed one second.

In some embodiments, the pulse duration is set so as not to exceed a single heartbeat duration (a single cardiac cycle) of the patient. Performing ablation in a single heartbeat is advantageous, for example, in that it is considerably easier to maintain the catheter stable for the duration of the procedure. In an embodiment, processor 41 pre-measures the heartbeat period of the specific patient being treated, and ensures that the pulse duration does not exceed the pre-measured heartbeat duration. Alternatively, the pulse duration may be set to be shorter than a global duration (e.g., some sub-second duration) that is suitable generally for all patients.

Display 46 of system 20 may be configured to display to physician 26, by methods which are known in the art, the progress of the RF delivery to the electrode. The display of the progress may be graphical, such as a simulation of the dimensions of a respective lesion as it is produced by the ablation, and/or by way of an alphanumeric display.

During the RF delivery procedure, processor 41 uses temperature module 52 and contact force module 57 to perform a number of checks on the progress of the procedure. In some embodiments, temperature is checked (68), and if temperature exceeds the allowable maximal value according to Table I, the processor ceases delivery of power and halts the ablation procedure, at an ablation termination step 72. Additionally or alternatively, contact force is checked (70), and if contact force falls below a prespecified value, the processor ceases delivery of power and halts the ablation procedure, at an ablation termination step 72.

The example flow chart shown in FIG. 2 is chosen purely for the sake of conceptual clarity. The present embodiment also comprises additional steps of the algorithm, such as checking a flow of irrigation, which have been omitted from the disclosure herein purposely on order to provide a more simplified flow chart.

Although the embodiments described herein mainly address cardiac applications, the methods and systems described herein can also be used in ablating other organs of the body, such as in renal and prostate ablation.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method of body tissue ablation, the method comprising:
   (a) defining an ultrahigh-power ultrashort-duration (UPUD) radiofrequency (RF) ablation protocol that specifies an ablation signal having (i) a target ablation power of at least 400 Watts and (ii) comprising setting the pulse duration to between 0.5 second and 0.9 second, for creating a specified lesion in tissue in a body of a patient, the tissue including cardiac tissue;
   (b) making contact between an ablation probe and the tissue; and
   (c) using the ablation probe, applying the ablation signal to the tissue according to the UPUD RF ablation protocol, which delivers the ablation signal having the specified target ablation power and duration.

2. The method according to claim 1, defining the UPUD RF ablation protocol comprising setting the pulse duration to not exceed a single heartbeat period of the patient.

3. The method according to claim 1, and comprising, during application of the ablation signal:
(a) monitoring a temperature in a vicinity of the tissue; and
(b) if the monitored temperature exceeds a predefined maximal temperature, halting the ablation signal.

4. The method according to claim 1, and comprising, during application of the ablation signal:
(a) monitoring a contact force that the probe exerts on the tissue; and
(b) if the monitored contact force falls below a prespecified value, halting the ablation signal.

5. The method according to claim 1, further comprising inserting the ablation probe through a blood vessel prior to the act of making contact between the ablation probe and the tissue.

6. The method according to claim 1, the specified lesion being selected from a low-depth lesion or a medium-depth lesion, the act of defining the UPUD RF ablation protocol comprising setting the pulse duration to between 0.5 second and 0.7 second in response to the specified lesion being the low-depth lesion, the act of defining the UPUD RF ablation protocol comprising setting the pulse duration to between 0.8 second and 0.9 second in response to the specified lesion being the medium-depth lesion.

7. A system for body tissue ablation, the system comprising:
(a) a memory, which is configured to store values of an ultrahigh-power ultrashort-duration (UPUD) ablation protocol that specifies an ablation signal having (i) a target ablation power of at least 400 Watts and (ii) a pulse duration that does not exceed three seconds, for creating a specified lesion in tissue in a body of a patient;
(b) an ablation probe, which is configured to make contact with the tissue;
(c) an ultrahigh-power ultrashort-duration (UPUD) generator, which is configured to generate the ablation signal; and
(d) a processor, which is programmed to control the generator and the ablation probe to apply the ablation signal to the tissue according to the UPUD protocol, which delivers the ablation power having the specified target ablation power and duration, the pulse duration being between 0.5 second and 0.9 second.

8. The system according to claim 7, the pulse duration not exceeding a single heartbeat period of the patient.

9. The system according to claim 7, the processor being further configured to control the probe, during application of the ablation signal, to:
(i) monitor a temperature in a vicinity of the tissue; and
(ii) if the monitored temperature exceeds a predefined maximal temperature, halt the ablation signal.

10. The system according to claim 7, the processor being further configured to control the probe, during application of the ablation signal, to:
(i) monitor a contact force that the probe exerts on tissue; and
(ii) if the monitored contact force falls below a prespecified value, halt the ablation signal.

11. The system according to claim 7, the ablation probe being sized and configured for insertion through a blood vessel into a chamber of a heart of the patient.

12. The system according to claim 7, the specified lesion being selected from a low-depth lesion or a medium-depth lesion, the pulse duration being between 0.5 second and 0.7 second when the specified lesion is the low-depth lesion, the pulse duration being between 0.8 second and 0.9 second when the specified lesion is the medium-depth lesion.

13. A method of cardiac tissue ablation, the method comprising:
(a) defining an ultrahigh-power ultrashort-duration (UPUD) radiofrequency (RF) ablation protocol that specifies an ablation signal having (i) a target ablation power of at least hundreds of 400 Watts and (ii) comprising setting the pulse duration to between 0.5 second and 0.9 second, for forming a specified lesion in tissue in a heart of a patient;
(b) inserting a catheter through a blood vessel into a chamber of the heart, the catheter including at least one distal tip electrode;
(c) making contact between the at least one distal tip electrode and the tissue; and
(d) applying the ablation signal to the tissue via the at least one distal tip electrode according to the UPUD RF ablation protocol to thereby form the specified lesion in the tissue.

14. The method according to claim 13, further comprising measuring a heartbeat period of the patient, the act of defining the UPUD RF ablation protocol comprising setting the pulse duration based on the measured heartbeat period of the patient.

15. The method according to claim 13, the specified lesion being selected from a low-depth lesion or a medium-depth lesion, the act of defining the UPUD RF ablation protocol comprising setting the pulse duration to between 0.5 second and 0.7 second in response to the specified lesion being the low-depth lesion, the act of defining the UPUD RF ablation protocol comprising setting the pulse duration to between 0.8 second and 0.9 second in response to the specified lesion being the medium-depth lesion.

16. The method according to claim 13, the at least one distal tip electrode comprising a plurality of distal tip electrodes, the specified lesion including a ring of specified lesions.

* * * * *